United States Patent [19]

Wier et al.

[11] Patent Number: 5,039,794

[45] Date of Patent: Aug. 13, 1991

[54] TUMOR EGRESS FACTOR AND PROCESSES FOR PRODUCING THE SAME

[75] Inventors: Marjorie L. Wier, Columbia, Md.; Joseph E. De Larco, Chesterfield, Mo.

[73] Assignee: Otsuka Pharmaceutical Co., Ltd., Tokyo, Japan

[21] Appl. No.: 96,576

[22] Filed: Sep. 15, 1987

Related U.S. Application Data

[63] Continuation-in-part of Ser. No. 909,356, Sep. 19, 1986, abandoned.

[51] Int. Cl.$^5$ .......................... C07K 15/06; C07K 3/28
[52] U.S. Cl. .................................. 530/399; 530/350; 530/351; 530/380; 530/395; 530/413; 530/414; 530/415; 530/416; 530/417
[58] Field of Search ............... 530/350, 828, 399, 413, 530/415, 414, 417, 416, 351, 395

[56] References Cited

PUBLICATIONS

Alitalo et al., EMBO J., 6(5), 1213–18, (1987).
DeLarco et al., PNAS (U.S.A.), 82, 5015–19, (Aug. 1985).
Liotta et al., PNAS (U.S.A.), 83, 3302–6, (May 1986).

*Primary Examiner*—Margaret Moskowitz
*Assistant Examiner*—Jeff Kushan
*Attorney, Agent, or Firm*—Sughrue, Mion, Zinn, Macpeak & Seas

[57] ABSTRACT

A novel cell scattering factor, i.e., tumor egress factor (hereinafter "egressin") isolated from a clone derived from a human metastatic melanoma (M3827) which possesses a loose colony morphology and from a human monocytic cell line (U937) and processes for producing the same. Egressin is useful for the production of immunological reagents for the detection and treatment of metastatic lesions, for aiding in the transport of drugs across the blood-brain barrier, and for aiding in the control of the inflammatory response.

10 Claims, 4 Drawing Sheets

TUMOR EGRESS FACTOR AND PROCESSES FOR PRODUCING THE SAME

CROSS-REFERENCE TO RELATED APPLICATIONS

The present invention is a Continuation in-Part Application of U.S. patent application Ser. No. 909,356, filed Sept. 19, 1986 now abandoned.

FIELD OF THE INVENTION

The present invention relates to a novel cell scattering factor. i.e., tumor egress factor (hereinafter "egressin") isolated from a clone derived from a human metastatic melanoma (M3827) which possesses a loose colony morphology and from a human monocytic cell line (U937) and processes for producing the same. Egressin is useful for the production of immunological reagents for the detection and treatment of metastatic lesions, for aiding in the transport of drugs across the blood-brain barrier, and for aiding in the control of the inflammatory response.

BACKGROUND OF THE INVENTION

A cell scattering factor has been isolated from the conditioned media of human embryo lung fibroblasts. This factor is assayed using either human mammary epithelial cells obtained from human milk samples or using a dog kidney epithelial cell line (MDCK). This assay measures the disassociation of the desmosomes between epithelial cells grown as islands in monolayers. This factor has a molecular weight of approximately 55,000 daltons and is a heat and acid labile protein (see Stoker, M., *J. Cell. Physiol.*, 121:174–183 (1984); Stoker, M. et al., *J. Cell Sci.*, 77:209–233 (1985) and Stoker, M. et al, *Nature* 327:239–242 (1987)).

A cell scattering factor has also been isolated from a human melanoma cell line (A2058). This factor is assayed using a human melanoma cell line (A2058) as indicator cells for the presence of the factor. This assay measures chemotaxis of the human melanoma cell line (A2058) (see Liotta, L. A. et al, *Proc. Natl. Acad. Sci., USA*, 83:3302–3306 (1986)). This cell scattering factor is thought to be the same factor as that described by Stoker, M., *J. Cell. Physiol.*, 121:174–183 (1984); Stoker, M. et al. *J. Cell Sci.*, 77:209–233 (1985) and Stoker. M et al, *Nature*, 327:239–242 (1987).

The observations that transformed cells grow as loosely associated clumps of cells and the normal rat kidney (NRK) colonies induced by the combination of epidermal growth factor (hereinafter "EGF") and tumor growth factor (hereinafter "TGF")-β consist of tightly associated aggregates of cells, suggested that there might be other ectopic factors released by transformed cells that were able to confer a loose colony morphology and that such factors might play a role in determining the metastatic potential of transformed cells.

Using the above rationale, i.e., that ectopic factors released by tumor cells can contribute to their expressed phenotypes, clones of a human metastatic tumor cell line were selected for a loose colony morphology, expecting that the colonies with loose morphologies would be producing factors that contributed to the expressed morphology.

As a result, it was ascertained that one clone. i.e., M3827 clone 3 (ATCC No. CRL 9193) released a factor that was able to induce a loose colony morphology in a normal rat kidney fibroblast clone (NRK-49F) (ATCC No. CRL 1570). This factor has been designated tumor egress factor or egressin and has been found to coelute with a factor possessing EGF-like activity (TGF-α) having an apparent molecular weight of 25,000 daltons in 1.0M acetic acid. (See DeLarco, J. E. et al, *Proc. Natl. Acad. Sci., USA*, 82:5015–5019 (1985) and DeLarco, J. E. et al, *Molecular Cell Biology*, 5:101–106 (1987).)

Inflammatory cells such as monocytes and granulocytes also are believed to move between cell compartments, disrupting cell junctions and exhibiting increased motility. Thus, a supernatant from a human monocyte cell line (U937) (ATCC No. CRL 1593), activated into the microphage differentiation pathway, was examined in the present invention for egressin-like activity. It has been ascertained in the present invention that this cell line also produces egressin.

SUMMARY OF THE INVENTION

The present invention was developed in part, in order to obtain a method of purifying egressin for M3827 clone 3 (ATCC No. CRL 9193) so that it is free of the factor possessing EGF-like activity and from other impurities, thereby providing egressin in a useful form for the production of immunological reagents for the detection and treatment of metastatic lesions, for aiding in the transport of drugs across the blood-brain barrier and for aiding in the control of the inflammatory response.

The present invention was also developed, in part, in order to obtain a method for purifying egressin from the U937 (ATCC No. 1593) human monocyte cell line thereby providing egressin in a useful form for the production of immunological reagents for the detection and treatment of metastatic lesions, for aiding in the transport of drugs across the blood-brain barrier and for aiding in the control of the inflammatory response.

Thus, an object of the present invention is to provide a novel cell scattering factor useful for the production of immunological reagents for the detection and treatment of metastatic lesions.

Another object of the present invention is to provide a novel cell scattering factor useful for aiding in the transport of drugs across the blood-brain barrier.

Still another object of the present invention is to provide a novel cell scattering factor useful for aiding in the control of the inflammatory response.

In one embodiment, the above-described objects of the present invention have been met by essentially pure egressin having the following properties:

(1) an apparent molecular weight of approximately 10,000 daltons as determined by SDS-PAGE;
(2) it is a basic protein;
(3) it is stable when heated at 56° C. for 30 minutes;
(4) it is stable at about pH 3.0 to about pH 10.0;
(5) it is active in inducing a loose colony morphology in normal rat kidney fibroblasts;
(6) it is active in effecting migration of normal rat kidney epithelial and fibroblast cells out of monolayer colonies thereof; and
(7) it is an indirect mitogen.

In another embodiment, the above described objects of the present invention have been met by egressin which is produced by the process comprising the following steps:

(1) culturing human metastatic melanoma M3827 clone 3 (ATCC No. CRL 9193) in serum-free media;

(2) collecting the resulting serum-free conditioned media;

and, additionally, the following steps, which can be carried out in any sequence, (3) carrying out molecular weight separation in the presence of 1.0M acetic acid and isolating the approximately 25,000 molecular weight fraction(s) containing egressin activity:

(4) carrying out cation-exchange separation and isolating the basic fraction(s) containing egressin activity;

(5) carrying out hydroxyapitite chromatography and isolating the tightly-bound fraction(s) containing egressin activity; and (6) carrying out hydrophobic separation and isolating the hydrophobic fraction(s) containing egressin activity, so as to obtain egressin purified at least about 10,000 fold.

In still another embodiment, the above described objects of the present invention have been met by egressin which is produced by the process comprising the following steps:

(1) culturing human monocytic cell line U937 (ATCC No. CRL 1593) in serum-free media and in the presence of a differentiation-inducing agent;

(2) collecting the resulting serum-free conditioned media;

and, additionally the following steps, which can be carried out in any sequence, (3) carrying out cation-exchange separation and isolating the basic fraction(s) containing the egressin activity;

(4) carrying out molecular weight separation in the presence of 1.0M acetic acid and isolating the approximately 25,000 molecular weight fraction(s) containing egressin activity;

(5) carrying out cation-exchange separation and isolating the basic fraction(s) containing egressin activity; and (6) carrying out hydrophobic separation and isolating the hydrophobic fraction(s) containing egressin activity.

so as to obtain egressin purified at least about 80,000 fold.

DETAILED DESCRIPTION OF THE INVENTION

Figure 1:
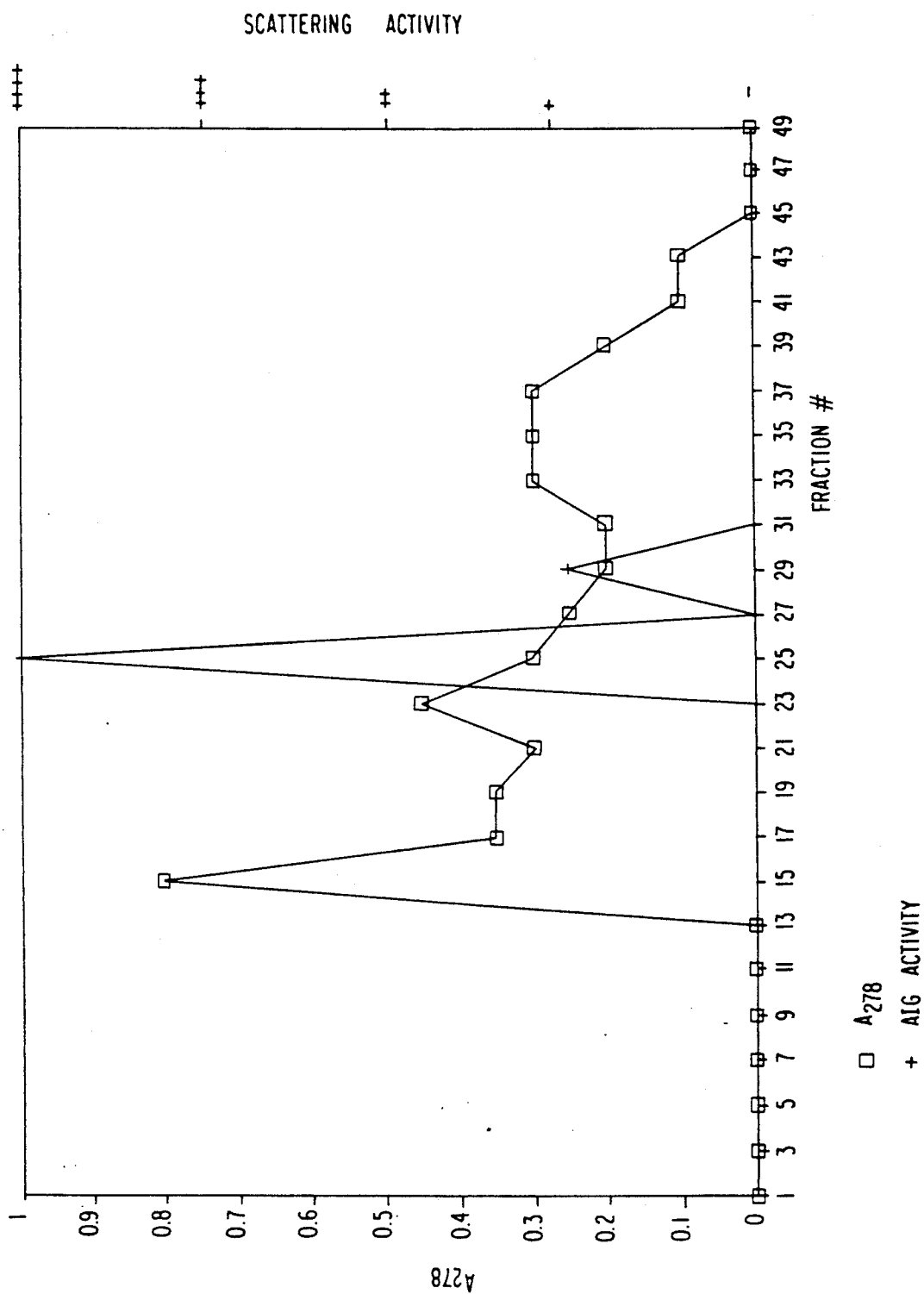
FIG. 1 shows molecular weight chromatography of human metastatic melanoma M3827 clone 3 serum-free conditioned media on a Bio-Gel P-60 column in the presence of 1.0M acetic acid, and the resulting egressin activity assayed in an anchorage independent growth assay.

As discussed above, in one embodiment, the above-described objects of the present invention have been met by essentially pure egressin having the following properties:

(1) an apparent molecular weight of approximately 10,000 daltons as determined by SDS-PAGE;

(2) it is a basic protein;

(3) it is stable when heated at 56° C. for 30 minutes:

(4) it is stable at about pH 3.0 to about pH 10.0;

(5) it is active in inducing a loose colony morphology in normal rat kidney fibroblasts;

(6) it is active in effecting migration of normal rat kidney epithelial and fibroblast cells out of monolayer colonies thereof; and (7) it is an indirect mitogen.

In another embodiment, the above-described objects of the present invention have been met by egressin which is produced by the process comprising the following steps:

(1) culturing human metastatic melanoma M3827 clone 3 (ATCC No. CRL 9139) in serum-free media;

(2) collecting the resulting serum-free conditioned media;

and, additionally, the following steps, which can be carried out in any sequence, (3) carrying out molecular weight separation in the presence of 1.0M acetic acid and isolating the approximately 25,000 molecular weight fraction(s) containing egressin activity;

(4) carrying out cation-exchange separation and isolating the basic fraction(s) containing egressin activity;

(5) carrying out hydroxyapitite chromatography and isolating the tightly-bound fraction(s) containing egressin activity; and (6) carrying out hydrophobic separation and isolating the hydrophobic fraction(s) containing egressin activity.

so as to obtain egressin purified at least about 10,000 fold.

In still another embodiment, the above described objects of the present invention have been met by egressin which is produced by the process comprising the following steps:

(1) culturing human monocytic cell line U937 (ATCC No. CRL 1593) in serum-free media and in the presence of a differentiation-inducing agent;

(2) collecting the resulting serum-free conditioned media;

and, additionally the following steps, which can be carried out in any sequence, (3) carrying out cation-exchange separation and isolating the basic fraction(s) containing the egressin activity;

(4) carrying out molecular weight separation in the presence of 1.0M acetic acid and isolating the approximately 25,000 molecular weight fraction(s) containing egressin activity;

(5) carrying out cation-exchange separation and isolating the basic fraction(s) containing egressin activity; and (6) carrying out hydrophobic separation and isolating the hydrophobic fraction(s) containing egressin activity, so as to obtain egressin purified at least about 80,000 fold.

During development, cells from the neural crest must migrate from this site (compartment) to other locations (compartment) within the organism. Cells of neural crest origin give rise to the melanocytes (in the skin) and the gastrointestinal tract In an adult, a given population of differentiated functional cells is often derived from a pool of precursor cells found in a different tissue or compartment, e.g., the Langerhan's cells of the epidermis (final compartment) are derived from a precursor or pool of mesenchymal cells in the bone marrow (compartment of origin). Egressin is believed to facilitate the migration of cells from one compartment to another during development.

Furthermore, the fact that egressin is produced by tumor cells, as an ectopic peptide, is believed to allow the tumor cells to migrate away from the primary tumor to distant sites, thus allowing the establishment of secondary metastatic sites.

In addition, egressin is believed to have a role in normal inflammatory response, migration and motility of macrophages and granulocytes.

Egressin can be purified from the serum-free conditioned media of human metastatic melanoma M3827 clone 3 (ATCC No. CRL 9193) which possesses a loose colony morphology.

The human monocytic leukemia cell line U937 (ATCC No. CRL 1593), when pre-treated with a differentiation-inducing agent, possess a loose colony morphology. The serum-free conditioned medium of treated cells has also been found to be a source of egressin.

Examples of the differentiation-inducing agent include 12-O-tetradecanoyl-phorbol 13-acetate (hereinafter "TPA") and phytohemaglutinin. TPA can be employed in an amount of about 10 to 250 ng/ml, preferably about 100 ng/ml. Phytohemoglutinin can be employed in an amount of about 10 to 200 µg/ml, preferably about 100 µg/ml.

Little egressin activity is secreted during the first 24 hours after induction of the U937 cell line with the differentiation-inducing agent and secretion is maximal at 48 hours. Secretion of egressin activity from the U937 cell line can not be induced with inonomycin, lipopoligosaccharide or IL-1. These compounds are agents which can cause partial activation of macrophage function. This suggests that egressin production by the U937 cell line is part of a specific differentiation pathway and not a general activation event.

The purification of egressin from M3827 clone 3 is carried out by a series of unique separation steps. One separation step is based on molecular weight, another separation step is based on cation-exchange, still another separation step is based on the unknown mechanism of hydroxyapitite chromatography and yet still another separation step is based on hydrophobicity. The above described separation steps may be carried out in any sequence although it is preferred that they are carried out in the sequence in which they are listed in order to provide maximum resolution.

The purification of egressin from U937 is also carried out by a series of unique separation steps. Two separation steps are based on cation-exchange, one separation step is based on molecular weight and another separation step is based on hydrophobicity. In addition, it is also preferable to employ a hydroxyapitite separation step in the purification of egressin from U937. The above-described separation steps may be carried out in any sequence.

Molecular weight separation can be carried out using, for example, gel-filtration chromatography, sucrose gradient sedimentation, or polyacrylamide gel electrophoresis. Gel-filtration can be carried out using well known sizing columns such as Bio-Gel p-30, Bio-Gel P-60, Sephadex G-25, Sephadex G-50, Sephadex G-75 or TSK-HPLC. In the present invention, gel-filtration chromatography is preferred, particularly using Bio-Gel P-60, because it is mild and does not denature the protein, it is highly specific and gives good resolution in the molecular weight range of egressin, and it can be scaled up to purify relatively large quantities of protein.

Cation-exchange separation can be carried out using, for example, a Pharmacia Mono-S cation-exchange resin. Whatman CM-52 cellulose, Whatman sulfoethyl cellulose or a Zeta-SP preparation cartridge. In the present invention, cation-exchange chromatography using a Pharmacia Mono-S cation-exchange resin or a Zeta-SP preparation cartridge is preferred because of their large capacity.

Hydroxyapitite chromatography can be carried out using, for example. Bio-Rad or other hydroxyapitite resins or Bio-Rad "high performance hydroxyapitite" (hereinafter "HPHT"). In the present invention, Bio-Rad HPHT is preferred because it allows rapid separation.

Hydrophobic separation can be carried out using, for example, a number of reverse phase resins such as $C_2$, $C_4$, $C_6$, $C_8$, $C_{18}$, etc. In the embodiment of the present invention where egressin is purified from M3827 clone 3. $C_{18}$ HPLC chromatography is preferred because it gives excellent resolution in the separation of egressin from other activities released by M3827 clone 3, i.e., TGF-α and TGF-β. This method also allows rapid separation, i.e., in a matter of minutes, rather than hours. Further, in the embodiment of the present invention where egressin is purified from the U937 cell line. $C_4$ HPLC chromatography is preferred because of its large capacity.

Egressin activity can be measured by its ability to induce a loose colony morphology in an anchorage independent growth (hereinafter "AIG") assay of cells from the normal rat kidney fibroblast clone (NRK-49F) (ATCC No. CRL 1570). Egressin activity can also be measured by its ability to induce morphological changes, i.e., migration of cells out of a monolayer colony of the NRK-49F cells or dissociation of tight junctions in the normal rat kidney epithelial clone (NRK-52E) (ATCC No. CRL 1571) cultured as a monolayer on tissue culture dishes.

For AIG assays, NRK-49F cells (ATCC No. CRL 1570) are plated at about $2.5 \times 10^3$ cells per 35 mm dish in 1.25 ml of 0.36% (w/v) agar in Dulbecco's modified Eagles' medium (hereinafter "DMEM") containing 10% (v/v) calf serum and 1.0 ng/ml of each of TGF-α and TGF-β. Egressin induces a loose colony morphology in the soft agar colonies induced under these conditions. That is, the tightly associated colonies of NRK-49F cells induced by the combination of TGF-α and TGF-β are modulated to colonies of loosely associated cells by the addition of egressin (see DeLarco. J. E, et al, *Proc. Natl. Acad. Sci., USA*, 82:5015-5019 (1985)).

For monolayer colony assays. NRK-52E cells (ATCC No. CRL 1571) or NRK-49F cells (ATCC No. CRL 1570) are plated at about $1 \times 10^2$ cells/ml in 35 mm culture dishes in DMEM containing 10% (v/v) calf serum. The cells form small tightly associated colonies after five days in culture. Egressin disrupts the cell-cell interactions, induces migration of cells out from these colonies and changes cell morphology. That is, NRK-49F cells become elongated in the presence of egressin. The elongation is believed to be due to egressin-induced reorganization of actin filaments. Further, NRK-52E cells show ruffled ridges and extended pseudopods in the presence of egressin.

The monolayer colony assay is the preferred assay because it is more sensitive than the AIG assay and because it can be conducted more rapidly, i.e., on the order of 6-24 hours as compared to 3-4 days with the AIG assay.

In the present invention, all of the cells are cultured in a humidified incubator at 37° C. in 5% $CO_2$/95% air.

Egressin of the present invention has been found to be (1) heat stable, i.e., egressin activity persists after treatment at 56° C. for 30 minutes (although it is inactivated by heat treatment at 100° C. for 10 minutes); (2) acid stable, i.e., egressin activity persists after treatment in 1.0M acetic acid (pH 3.0) for several months when maintained at 4° C. (although it is sensitive at pH values lower than about 3.0): (3) egressin activity persists up to about pH 10.0; and (4) egressin is inactivated by 50% (v/v) acetonitrile:0.1% (v/v) trifluoroacetic acid (hereinafter "TFA").

Egressin activity is not inhibited by the protease inhibitors pepstatin and nitrophenyl guaidine benzoate-HCl. In fact, egressin activity is enhanced by the protease inhibitors soy bean trypsin inhibitor (Sigma Chemical Co.) and phenyl-methyl sulfonyl-fluoride. In addition, egressin activity is not affected by either urokinase nor streptokinase. All of these results suggest that egressin activity is not due to serine protease activity nor plasminogen activator activity, although other types of proteases cannot be ruled out.

Egressin activity is also destroyed by treatment with dithiothreitol and trypsin. These results suggest that egressin is a protein stabilized by disulfide bonds.

The cell scattering factor described by Stoker, M., *J. Cell. Physiol.*, 121:174-183 (1984); Stoker, M. et al, *J. Cell Sci.*, 77:209-233 (1985) and Stoker, M. et al, *Nature* 327:239-242 (1987) is not active in either the AIG assay or monolayer colony assay of the present invention nor is egressin found to be active in the assays described by Stoker, M., *J. Cell. Physiol.*, 121:174-183 (1984); Stoker, M. et al, *J. Cell Sci.*, 77:209-233 (1985) and Stoker, M. et al, *Nature*, 327:239-242 (1987).

Some of the differences between egressin and the cell scattering factor described by Stoker, M., *J. Cell. Physiol.*, 121:174-183 (1984); Stoker, M. et al, *J. Cell Sci.*, 77:209-233 (1985) and Stoker, M. et al, *Nature*, 327:239-242 (1987) are listed in Table I below.

TABLE I

| | Characteristics of Egressin of the Invention and Cell Scattering Factor | | |
|---|---|---|---|
| | Egressin of the Invention | | Cell Scattering |
| Cell source | human metastatic melanoma (M3827 clone 3) | human monocytic cell line (U937) | Factor human embryo lung fibroblasts |
| Active on Cell Type: | | | |
| normal rat kidney fibroblasts (NRK-49F) | yes | yes | no |
| normal rat kidney epithelial cells (NRK-52E) | yes | yes | no |
| human mammary epithelial cells | no | — | yes |
| bovine aortic endothelial cells | yes | yes | — |
| dog kidney epithelial cells | no | — | yes |
| SDS Molecular weight | 10,000 daltons | 10,000 daltons | 55,000 daltons |
| Stable at 56° C. for 30 Minutes | yes | yes | no |
| Stable at pH 3.0 to 10 | yes | yes | no |
| Basic or acidic protein | basic | basic | acidic |

Egressin is useful for the production of immunological reagents for the detection and treatment of metastatic lesions. As sued herein, "immunological reagents" mean antibodies. The antibodies include polyclonal or monoclonal antibodies which can be prepared by conventional techniques using egressin as the antigen (see *Handbook of Experimental Immunology*, Ed Weir, D.M., Vol. III (Blackwell Scientific Publications, 1978, Oxford, England).

The antibodies can be used for either (1) the detection (diagnostic) of a potentially metastatic lesion, for example, by a conventional competitive enzyme-linked immunoassay or radioimmunoassay which measures the presence of egressin in a serum sample or (2) treatment of an already existing metastatic lesion, for example, by administering intravenously the antibody in a therapeutically effective amount such that it will bind with egressin present in the serum thereby inactivating such so as to prevent the formation of additional metastatic sites or to effect regression of the present tumors.

Since egressin disperses endothelial cells in a monolayer colony assay, it should also act on the cell-cell junctions of the endothelial cells lining the blood vessels. The dissociation of these junctions would increase the permeability of the vessels and decrease the effectiveness of the blood-brain barrier. Thus, this property of egressin is believed to be useful for aiding in the transport of drugs across the blood-brain barrier for the treatment of certain conditions effecting the central nervous system. Examples of such conditions include infections or tumors of the central nervous system. That is, egressin is believed to be able to increase the entry of drugs such as antibiotics, in addition to antibodies and cells of the immune system, into the central nervous system to combat these infections. In this embodiment, an amount of egressin effective for the dissociation of the cell-cell junction of endothelial cells is administered intravenously alone (in the case of increasing the entry of antibodies or cells of the immune system into the central nervous system) or along with a therapeutically effective amount of the drug of choice (in the case of increasing the entry of drugs into the central nervous system).

Egressin can also be employed for aiding in control of the inflammatory response, i.e., migration of leukocytes from blood vessels into lesions. In an acute inflammatory response, granulocytes and monocytes circulating in the blood are activated or induced to differentiate. These activated cells adhere to the endothelium and migrate between the endothelial cell junctions and through the extra vascular tissues to the site of injury or infection. The activated inflammatory cells may produce and secrete egressin so as to disrupt the endothelial cell junctions and tissue structure. Thus, egressin can be used to enhance the movement of inflammatory cells from the blood vessels to the site of injury by therapeutically administering egressin at the site of injury. Alternatively, an antibody to egressin could be administered intravenously to block migration of inflammatory cells and to reduce the detrimental effects of inflammation.

Egressin purified in the present invention has a specific activity of greater than 10,000 units/ml, preferably greater than 100,000 units/ml. A "unit" is the amount of egressin required to give a half-maximal response.

The following examples are provided for illustrative purposes only and are no way intended to limit the scope of the present invention.

EXAMPLE 1

Purification of Egressin from M3827 clone 3

(A) Growth of M3827 clone 3 and Preparation of Serum-free Conditioned Media

Egressin was purified from serum-free media conditioned by the human metastatic melanoma M3827 clone 3. More specifically, the melanoma cells were grown to a high density ($2 \times 10^8$ to $1 \times 10^9$) in roller bottles in the presence of DMEM containing 4.5 grams per liter of glucose and 10% (v/v) calf serum. Serum components were removed by incubating the cells in two changes of serum-free media, then the cells were incubated in fresh serum free media for 48 hours at 37° C. The resulting serum-free conditioned media (hereinafter "SF-CM") was subjected to low speed centrifugation (500×g for 5 minutes at 10° C.) to remove cells followed by high speed centrifugation (35,000×g for 60 minutes at 10° C.) to remove readily sedimentary subcellular particles. The resulting SF-CM was dialyzed at 4° C., against four changes of 5 volumes each of 1.0M acetic acid, pH 3.0 and lyophilized. The lyophilized material was then suspended in 1/100th the volume of 1.0M acetic acid, pH 3.0 and clarified by centrifugation at 35,000×g for 90 minutes at 10° C.

(B) Molecular Weight Separation

Molecular weight separation was carried out using gel-filtration chromatography. Gel-filtration chromatography was performed on the clarified resulting supernatant using a Bio-Gel P 60 column (2.6 cm×95 cm) which was packed and equilibrated with 1.0M acetic acid, pH 3.0. Bio-Gel P-60 is a porous polyacrylamide bead for high resolution gel-filtration. The gel is prepared by copolymerization of acrylamide and N,N'-methylene-bis-acrylamide. The column was calibrated prior to use with molecular weight standards.

More specifically, 10 ml of the clarified supernatant described above was loaded onto the column and the chromatogram was developed in 1.0M acetic acid, pH 3.0 at a flow rate of 15 ml/hr at 25° C. 7.5 ml fractions were collected. The elution was monitored by absorbance of $A_{278}$. 75 μl aliquots from odd numbered fractions were lyophilized in the presence of 100 μg of bovine serum albumin (hereinafter "BSA") as a carrier. These aliquots were then suspended in 500 μl of DMEM containing 0.5% (v/v) calf serum and assayed for egressin activity using the AIG assay without added growth factors as described above. The results are shown in FIG. 1. In FIG. 1, "—" indicates no response, i.e., where all of the cells remain as single cells, while "+ + + +" indicates the maximum response, i.e., where colonies of loosely associated cells are formed.

As the results in FIG. 1 demonstrate, egressin activity was found to elute in fractions 23-27 with an apparent molecular weight of approximate)y 25,000 daltons. At this point, the egressin activity had been purified approximately 24 fold over that found in the initial SF-CM.

(C) Cation-Exchange Separation

Figure 2:
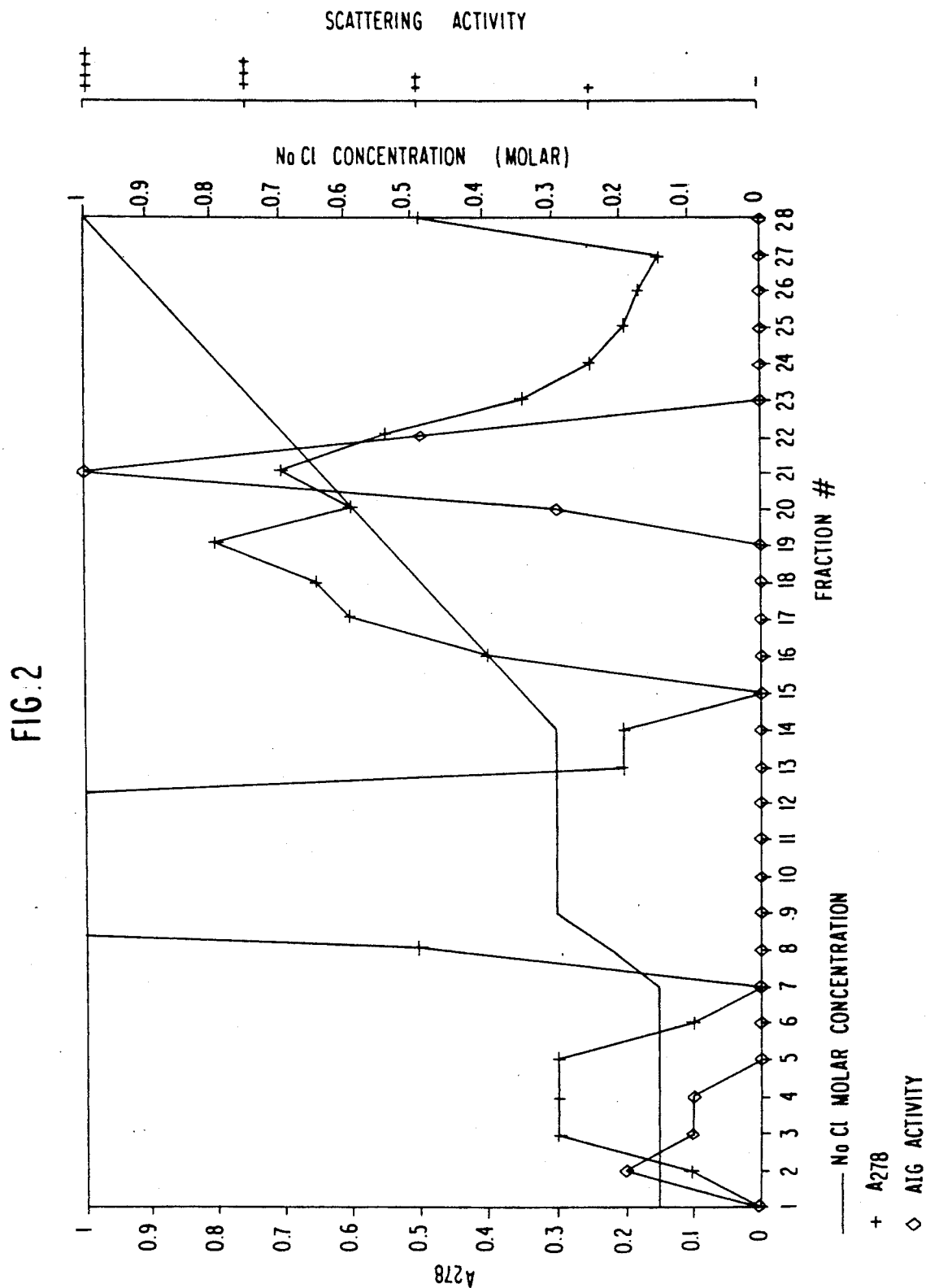
FIG. 2 shows cation-exchange chromatography of the egressin activity containing fractions, obtained from the Bio-Gel P-60 column of FIG. 1, on a Pharmacia Mono-S column, and the resulting egressin activity assayed in an anchorage independent growth assay.

Fractions 23-27 described above having an apparent molecular weight of approximately 25,000 daltons and containing egressin activity, were then pooled and dialyzed overnight against 0.025M sodium acetate buffer, pH 5.0 containing 0.15M NaCl. Next, the pooled fractions were loaded onto a Pharmacia Mono-S column which had been equilibrated with 0.025M sodium acetate buffer, pH 5.0. Pharmacia Mono-S is a strong cation exchanger based on a beaded hydrophobic resin. The beads have a particle size of about 10 μ. The charge group on the resin is —$CH_2$—$SO_3^-$. The majority of the prqtein flowed through the column under these conditions. The bound proteins were eluted with a linear gradient of 0-1.0M NaCl having a slope of 22 mM/min and run at 1.0 ml/min. 2.0 ml fractions were collected. The flow through was monitored by absorbance at $A_{278}$. 20 μl aliquots from each fraction were lyophilized in the presence of 100 μg of BSA, suspended in 500 μl of DMEM containing 0.5% (v/v) calf serum and assayed for egressin activity using the AIG assay without added growth factors as described above. The results are shown in FIG. 2. In FIG. 2, "—" indicates no response, i.e., where all of the cells remain as single cells, while "+ + + +" indicates the maximum response, i.e., where colonies of loosely associated cells are formed.

As the results in FIG. 2 demonstrate, egressin activity was found to elute in fractions 20-22, i.e., between 0.6M and 0.7M NaCl. At this point, the egressin activity had been purified approximately 480 fold over that found in the initial SF-CM.

(D) Hydroxyapitite Separation

Figure 3:
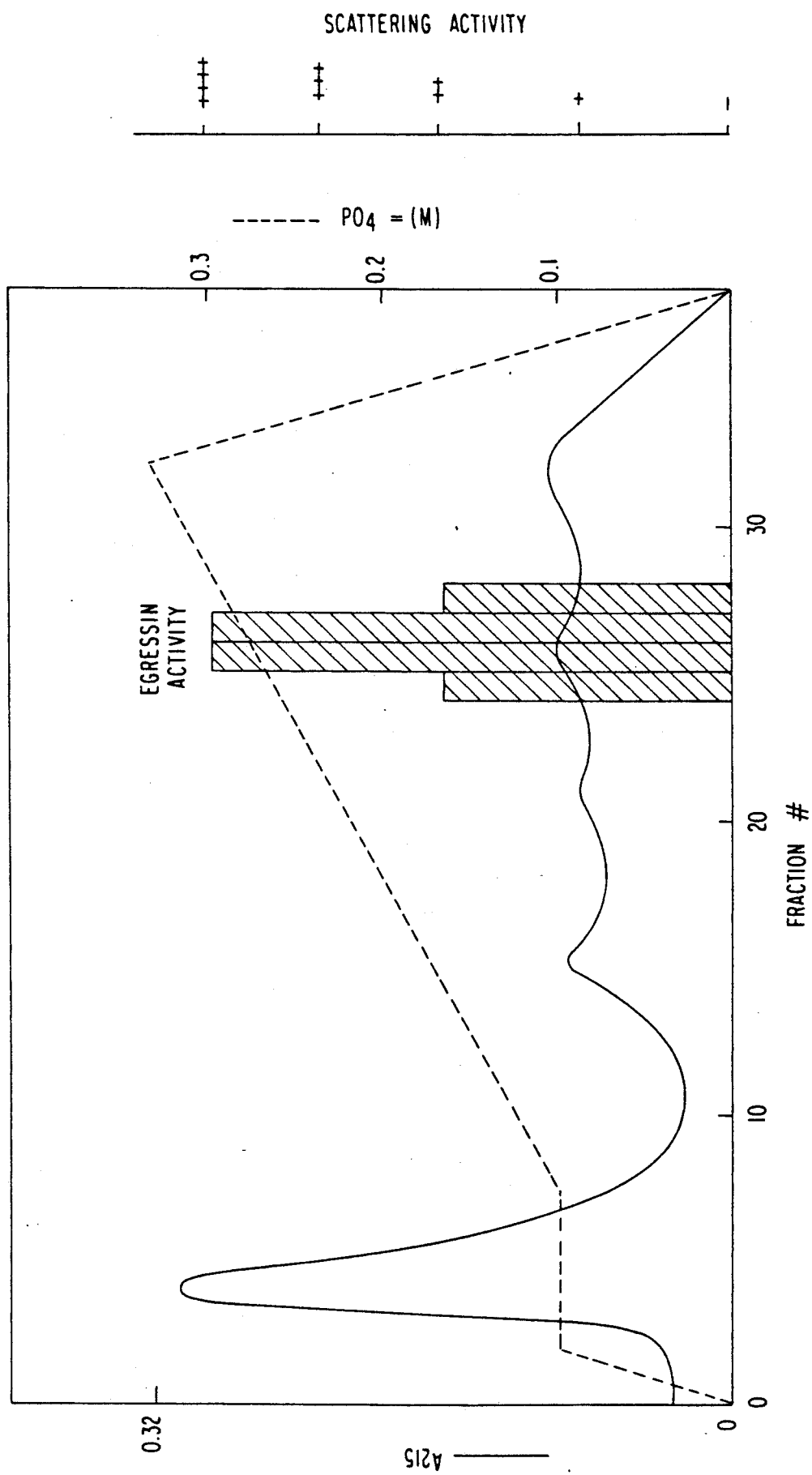
FIG. 3 shows hydroxyapitite chromatography of the egressin activity containing fractions obtained from the Pharmacia Mono-S column of FIG. 2, on a Bio-Rad HPHT column and the resulting egressin activity assayed in a monolayer colony assay.

Fractions 20-22 described above containing egressin activity were pooled and loaded onto a Bio-Rad HPHT column which had been equilibrated with 10 mM sodium phosphate buffer, pH 6.8. Bio-Rad HPHT is a beaded resin and has an unknown mechanism and separation. The majority of the protein was eluted from the column by washing with 100 mM sodium phosphate buffer, pH 6.8. The tightly bound proteins were eluted with a linear gradient of 100-300 mM sodium phosphate buffer, pH 6.8 over 60 minutes with a flow rate of 0.5 ml/min. 2.0 ml fractions were collected. The elution was monitored by absorbance at $A_{215}$. 100 ml aliquots were lyophilized in the presence of 100 μg of BSA, resuspended in 500 μl of DMEM containing 0.5% (v/v) calf serum and then assayed for egressin activity using the monolayer assay as described above. The results are shown in FIG. 3. In FIG. 3, "—" indicates no response, i.e., where all of the cells remain in tight colonies with intact junctions, while "+ + + +" indicates the maximum response, i.e., where only single cells are present, i.e., where no cells are touching.

As the results in FIG. 3 demonstrate, the majority of egressin activity was found to elute in fractions 27-29, i.e., between 250 and 300 mM sodium phosphate buffer, pH 6.8. At this point, the egressin activity was purified approximately 2,000 fold over that found in the initial SF-CM.

(E) Hydrophobic Separation

Figure 4:
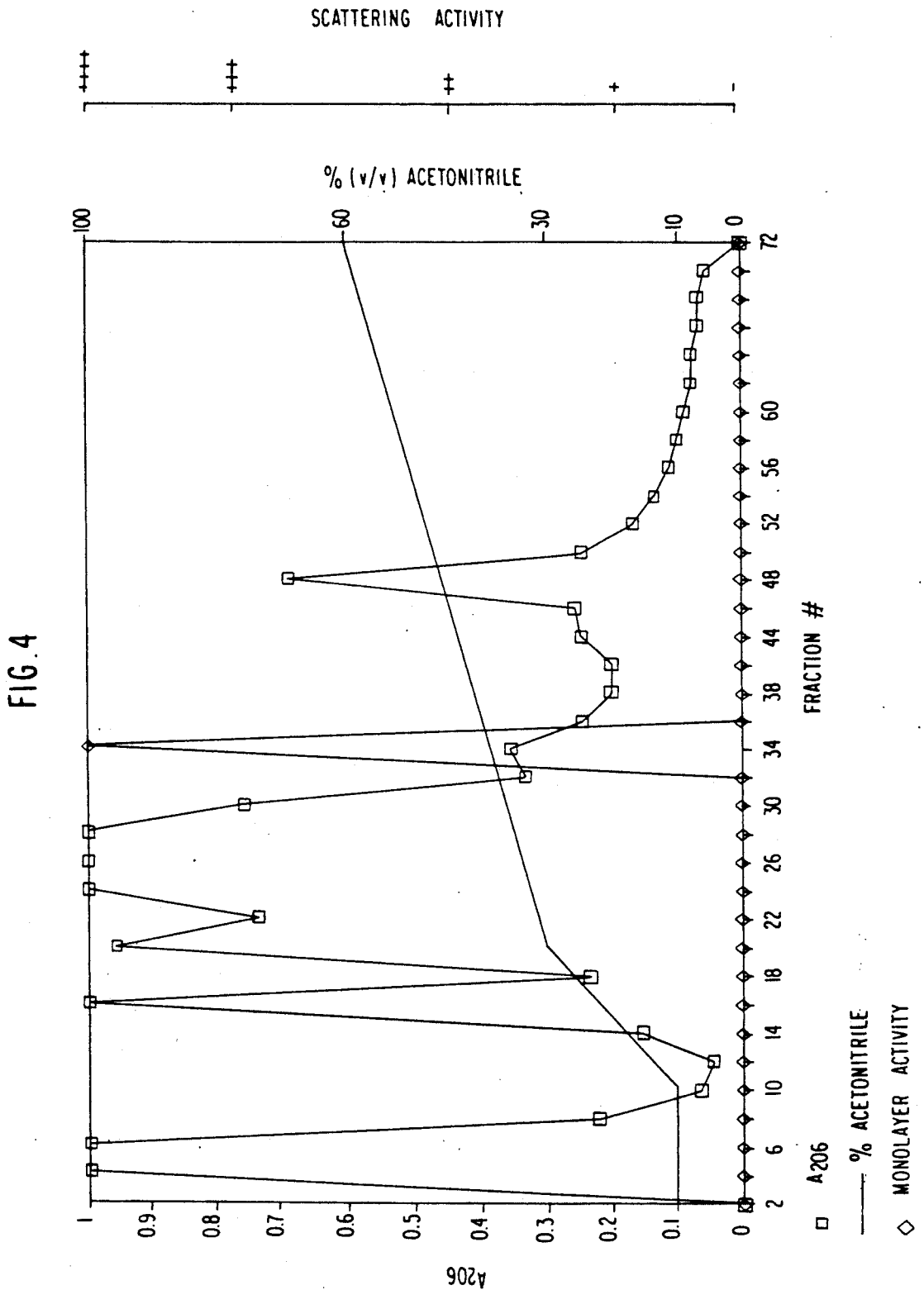
FIG. 4 shows hydrophobicity chromatography of the egressin activity containing fractions, obtained from the Bio-Rad HPHT column of FIG. 3, on a Vydac $C_{18}$ HPLC column, and the resulting egressin activity assayed in a monolayer colony assay.

Fractions 27-29 described above from the HPHT column containing egressin activity were then pooled and diluted 1:3 with HPLC grade distilled water containing 0.1% (v/v) TFA and the pH was adjusted to 2.5 with 1.0M HCl. Next, the diluted fractions were loaded onto a Vydac $C_{18}$ HPLC column. Vydac $C_{18}$ HPLC consists of a $C_{18}(-(CH_2)_{17}-CH_3)$ hydrophobic bonded phase on a 300 Å pore-size, 10 μ spherical silica bead. The column was equilibrated with 0.1% (v/v) $TFA:H_2O$ and run at 1.0 ml/min. 1.0 ml fractions were collected. Loosely bound proteins were eluted with a step to 30% (v/v) acetonitrile:0.1% (v/v) $TFA:H_2O$. The more tightly bound proteins were eluted with a linear gradient of 30-60% (v/v) acetonitrile:0.1% (v/v) $TFA:H_2O$ developed at 0.5% (v/v)/min, and the column was washed with 100% (v/v) acetonitrile:0.1% (v/v) TFA. The elution was monitored by absorbance at $A_{206}$. 50 μl aliquots from each fraction were lyophilized in the presence of 100 μg of BSA, resuspended in 500 μl of DMEM containing 0.5% (v/v) calf serum and then assayed for egressin activity using the monolayer assay as described above. The results are shown in FIG. 4. In FIG. 4. "—" indicates no response, i.e., where all of the cells remain in tight colonies with intact junctions, while "++++" indicates the maximum response, i.e., where only single cells are present, i.e., where no cells are touching.

As the results in FIG. 4 demonstrate, the majority of egressin activity was found to elute in fractions 33-35, i.e., between 32 and 34% (v/v) acetonitrile. At this point, the egressin activity had been purified approximately 10,000 fold over that found in the initial SF-CM.

EXAMPLE 2

Purification (A) of Egressin From U937

(A) Growth of U937 and Preparation of Serum-Free Condition Media

Egressin was purified from serum-free media conditioned by the human monocytic cell line U937 which was pre-treated with 12-O-tetradecanoyl-phorbol 13-acetate at 37° C. for 48 hours. More specifically, the human monocytic cells were grown to a density of about $1 \times 10^6$ cells per ml in roller bottles in the presence of RPMI media containing 10% (v/v) calf serum. Serum components were removed by centrifugating the cells (500×g for 5 min at 25° C.). Then the cells were incubated in fresh serum-free RPMI media for 94 hours at 37° C. in the presence of about 100 ng/ml of TPA. The cells were then centrifuged as above and resuspended in serum-free RPMI media for 24 hours at 37° C. in the presence of about 100 ng/ml of TPA. The resulting SF-CM was subjected to low speed centrifugation (500×g for 5 min at 25° C.) to remove the cells. The resulting SF-CM was acidified with 6.0 N HCl to pH 5.5 and clarified by centrifugation (35,000×g for 90 min at 10° C.).

(B) Cation-exchange Separation

Preparative cation-exchange chromatography was performed on the SF-CM described above using a Zeta-SP preparation cartridge which was equilibrated with 0.025M sodium acetate buffer, pH 5.5. Approximately 20 liters of SF-CM was passed over the Zeta-SP preparation cartridge at a flow rate of approximately 5.0 ml/min. The eluent was monitored by absorbance at $A_{278}$. The cartridge was washed with 0.025M sodium acetate buffer, pH 5.5 until absorbance was returned to background levels. The column was then washed with 0.025M sodium acetate buffer, pH 5.5 containing 1.0M NaCl and the eluent was collected until the absorbance again returned to background. Approximately 400 ml were collected. Finally, the cartridge was washed with 0.025M sodium acetate buffer, pH 5.5 containing 2.0M NaCl until the background returned to zero. Aliquots of the flow through, 1.0M NaCl pool and the 2.0M NaCl were dialyzed against 1.0M acetic acid, pH 3.0, lyophilized, resuspended in 500 μl of DMEM containing 0.5% (v/v) calf serum and tested for egressin activity using the monolayer assay as described above. Egressin activity was found to elute in the 1.0M NaCl pool. At this point, the egressin activity was purified approximately 50 fold over that found in the initial SF-CM.

(C) Molecular Weight Separation

The 1.0M NaCl pool described above was dialyzed at 4° C., against four changes at 5 volumes each of 1.0M acetic acid, pH 3.0 and then lyophilized. The resulting material was resuspended in 10 ml of 1.0M acetic acid, pH 3.0 and subjected to high speed centrifugation (35,000×g at 10° C. for 45 minutes) to remove particulates. The clarified supernatant was loaded onto a Bio-gel P-60 column (2.6 cm×95 cm) which was equilibrated with 1.0M acetic acid, pH 3.0. The chromatogram was developed in 1.0M acetic acid, pH 3.0 at a flow rate of 15 ml/hr at 25° C. 7.5 ml fractions were collected. The eluent was monitored by absorbance at $A_{278}$. 100 μl aliquots of the fractions Were lyophilized in the presence of 100 μg of BSA, then resuspended in 500 μl of DMEM containing 0.5% (v/v) calf serum and assayed for egressin activity using the monolayer assay as described above. Egressin activity was found to elute in fractions with an apparent molecular weight of approximately 25,000 daltons. At this point, the egressin activity was purified approximately 2,000 fold over that found in the initial SF-CM.

(D) Cation-exchange Separation

The fractions obtained above having an apparent molecular weight of 25,000 containing egression activity in the Bio-gel P-60 column were pooled, lyophilized and resuspended in 10 ml of 0.025M sodium acetate buffer, pH 5.0 containing 0.15M NaCl. The sample was centrifuged to remove particulates as described above and then loaded onto a Pharmacia Mono-S column which has been equilibrated with 0.025M sodium acetate buffer, pH 5.0. The column was washed with 0.025M sodium acetate buffer, pH 5.0 containing 0.3M NaCl until the absorbance of the eluent measured at $A_{278}$ returned to background. The remaining tightly bound proteins were eluted with a linear gradient of 0.3 to 1.0M NaCl having a slope of 22 mM NaCl/min and run at 1.0 ml/min. 50 μl aliquots from each fraction were lyophilized in the presence of 100 μg of BSA and then resuspended in 500 μl DMEM containing 0.5%

(v/v) calf serum and assayed for egressin activity using the monolayer assay described above. Egressin activity was found to elute primarily in fractions between 0.6M and 0.7M NaCl. At this point, the egressin activity was purified approximately 12,000 fold over that found in the initial SF-CM.

(E) Hydroxyapitite Separation

The fractions obtained above containing egressin activity were pooled and loaded onto a Bio-Rad HPHT column which had been equilibrated with 10 mM sodium phosphate buffer, pH 6.8. The majority of the protein was eluted from the column by washing with 100 mM sodium phosphate buffer, pH 6.8. The tightly bound proteins were eluted with a linear gradient of 100-300 mM sodium phosphate buffer, pH 6.8 over 60 minutes with a flow rate of 0.5 ml/min. 2.0 ml fractions were collected. The elution was monitored by absorbance at $A_{215}$. 100 µl aliquots were lyophilized in the presence of 100 µg of BSA, resuspended in 500 µl of DMEM containing 0.5% (v/v) calf serum and then assayed for egressin activity using the monolayer assay as described above. Egressin activity was found to elute between 250 and 300 mM sodium phosphate buffer, pH 6.8. At this point, the egressin activity was purified approximately 80,000 fold over that found in the initial SF-CM.

(F) Hydrophobic Separation

The fractions from the HPHT column containing egressin obtained above were pooled and the pH was adjusted to 2.5 with 1.0M HCl. The material was loaded onto a Vydac $C_4$ semi-preparative column equilibrated with 0.01% (v/v) $TFA:H_2O$. The eluent was monitored by absorbance at $A_{206}$. The column was washed with 0.01% (v/v) $TFA:H_2O$ until the absorbance returned to background. The more tightly bound proteins were eluted with a linear gradient of 25-35% (v/v) acetonitrile:0.1% (v/v) $TFA:H_2O$ developed over 100 minutes. 1.0 ml fractions were collected and 100 ml of 1.0M ammonium acetate was added to each fraction. 100 µl aliquots from the resulting fractions were lyophilized in the presence of 100 µg of BSA, resuspended in 500 µl of DMEM containing 0.5% (v/v) calf serum and then assayed for egressin activity using the monolayer assay described above. Egressin activity was found to elute approximately 29% (v/v) acetonitrile. At this point, the egressin activity was purified approximately 100,000 fold over that found in the initial SF-CM.

EXAMPLE 3

Purification (B) of Egressin From U937

(A) Growth of U937 and Preparation of Serum-Free Condition Media

Egressin was purified from serum-free media conditioned by the human monocytic cell line U937 which was pre-treated with TPA. More specifically, the human monocytic cells were grown to a density of about $1 \times 10^6$ cells per ml in a 75 liter fermentation vessel in the presence of RPMI media containing 7.0% (v/v) fetal calf serum. Prior to induction, serum components were removed by concentrating media containing the cells to approximately 10 liters using a Pro-stalk membrane filtration system then subjecting the cells to low speed centrifugation ($500 \times g$ for 5 min at 10° C.). The cell pellets were resuspended in fresh serum-free RPMI media in the presence of about 100 ng/ml of TPA and inoculated in a 40 liter fermenter. After 36 hrs of incubation at 37° C., the cells were removed by passing the media through a continuous flow α-Lavell centrifugation system. The resulting SF-CM was concentrated using a Pelicon concentration device employing 10,000 daltons cut-off filters. The SF-CM was concentrated approximately 40 fold to a final volume of about 1.0 liter. This material was acidified with 6.0N HCl to pH 5.5.

(B) Cation-exchange Separation

Preparative cation-exchange chromatography was performed on the SF-CM described above using a Zeta-SP preparation cartridge which was equilibrated with 0.025M sodium acetate buffer, pH 5.5. The conductivity of the SF-CM was adjusted with 0.025M sodium acetate buffer, pH 5.5 to be equal to or lower than that of a 0.025M sodium acetate buffer, pH 5.5, 0.15M NaCl solution. The resulting material was passed over the Zeta-SP preparation cartridge at a flow rate of approximately 5.0 ml/min. The cartridge was washed and the proteins were eluted as described in Example 2 above.

(C) Cation-exchange Separation

The 1.0M NaCl described above was adjusted with 0.025M sodium acetate, pH 5.5 so that its conductivity was approximately that of a 0.15M NaCl solution. The material was then loaded onto a Pharmacia Mono-S 10/10 semi-preparative cation-exchange column equilibrated with 0.025M sodium acetate buffer, pH 5.5 containing 0.3M NaCl. The eluent was monitored by absorbance at $A_{278}$. The column was run at 4.0 ml/min and 4.0 ml fractions were collected. The column was washed until the absorbance returned to background level. Then, proteins were eluted with a linear gradient of 0.3M NaCl to 1.0M NaCl over 35 minutes. 100 µl aliquots of odd numbered samples were diluted with 90 µl of DMEM containing 0.5% (v/v) calf serum and assayed for egressin activity using the monolayer assay described above. Egressin activity was found in fractions 28-31 corresponding to approximately 0.6-0.7M NaCl.

(D) Molecular Weight Separation

The fractions from the Mono-S column containing egressin activity were pooled and dialyzed against 1.0M acetic acid, pH 3.0. The dialyzed fractions were lyophilized and resuspended in 10 ml at 1.0M acetic acid, pH 3.0 and then subjected to high speed centrifugation as described above to remove particulates. The chromatogram was developed using a Bio-Gel P-60 column as described in Example 2 above. Egressin activity was assayed by the monolayer assay as described above and found to elute elute with an apparent molecular weight of approximately 25,000 daltons.

(E) Hydrophobic Separation

The fractions containing egressin activity from the Bio-gel P-60 column obtained above were loaded directly onto a Vydac $C_{18}$ column and developed as described in Example 2 above. Egressin activity was found to elute in fraction 39 at approximately 36% (v/v) acetonitrile.

In this purification process, steps (D) and (E) can be interchanged.

EXAMPLE 4

Amino Acid Analysis

The purified egressin obtained in Example 2 above was subjected to amino acid analysis as described in Roth, M., *Anal. Chem.*, 43:880–882 (1971). The results are set forth in Table II below.

TABLE II

| ASP | 10.7 |
|---|---|
| THR | 5.2 |
| SER | 6.7 |
| GLU | 14.8 |
| PRO | N.D. |
| GLY | 9.8 |
| ALA | 7.7 |
| CYS | N.D. |
| VAL | 5.4 |
| MET | 1.1 |
| ILE | 3.5 |
| LEU | 6.3 |
| TYR | 1.9 |
| PHE | 2.8 |
| LYS | [10] |
| HIS | 2.3 |
| TRP | N.D. |
| ARG | 5.0 |
| TOTAL | 93.2 |

The composition data described above is based on the assumption of a certain number of one residue and then the relative amounts of the others are determined. In this case, lysine was set to [10] and the remaining residues were calculated on relative amounts, assuming the total molecular weight to be about 10,000 daltons.

EXAMPLE 5

SDS-PAGE

Sodium dodecyl-sulfate polyacrylamide gel electrophoresis (SDS-PAGE) was performed as described in Laemnli, U.K., *Nature*, 227:680 (1970). The resulting gel was 15% (w/v) polyacrylamide. After electrophoresis, gels were stained for proteins with Coomassie Blue, then with silver using a commercially available reagent obtained from Bio-Rad. Molecular weight markers were used to standardize the gels.

Aliquots of fractions from each step in Example 3 were lyophilized and resuspended in sample buffer as described in Laemnli, supra, containing 10 mM DTT and subjected to gel electrophoresis. Gels and materials derived from the final steps of the purification showed a single band of molecular weight of approximately 10,000 daltons.

EXAMPLE 6

Assay for Growth Activity (A) Direct Mitogenic Assay

Growth activity was monitored by the uptake of $^3$H-thymidine into trichloroacetic acid precipitable material. More specifically, all of the cells shown in Table III below were plated in DMEM containing 10% (v/v) calf serum at $1 \times 10^4$ cells/well in 24 well plates. After 24 hours at 37° C., the medium was changed to DMEM containing 0.5% (v/v) calf serum. Cultures were incubated for 72 hours in this low serum media, then treated with the factors listed in Table III below.

EGF was employed at a concentration of 5.0 ng/ml in DMEM containing 0.5% (v/v) calf serum. 50 μl of fraction 22 from the chromatograph shown in FIG. 2 was lyophilized and suspended in 100 μl of DMEM containing 0.5% (v/v) calf serum or the 5.0 ng/ml EGF solution.

100 μl of 10% (v/v) calf serum, the EGF solution, the egressin solution or the egressin containing EGF solution was then added to the wells.

After culturing for 18 hours at 37° C., 100 μl of 0.01 μCi/ml of $^3$H-thymidine was added to each well and the cells were cultured for an additional 8 hours. The cultures were then rinsed twice with Waymouth's media containing 100 μg/ml cold thymidine at 4° C., and twice with Waymouth's media containing no additives. Next, the cells were rinsed with 10% (w/v) trichloroacetic acid at 4° C., and then solubilized with 0.5 ml of 0.1% (w/v) NaOH. The solubilized material was added to 5.0 ml of an aqueous based liquid scintillant (Safety-solve, Research Products Institute) and counted in a scintillation counter. The mitogenic index, expressed as the ratio of cpm incorporated in the presence of added factors/cpm incorporated in cultures receiving no added factors, is shown in Table III below. All experiments were done on duplicate wells.

TABLE III

| | Direct Mitogenic Assay | |
|---|---|---|
| Cell Type | Addition | Mitogenic Index |
| Swiss 3T3 | None | 1.00 |
| Fibroblasts | 10% Calf Serum | 2.44 |
| | EGF | 1.66 |
| | Egressin | 0.99 |
| | Egressin + EGF | 1.30 |
| NRK-49F | None | 1.00 |
| | 10% Calf Serum | 2.66 |
| | EGF | 4.36 |
| | Egressin | 1.11 |
| | Egressin + EGF | 1.90 |
| NRK-52E | None | 1.00 |
| | 10% Calf Serum | 6.38 |
| | EGF | 1.41 |
| | Egressin | 1.11 |
| | Egressin + EGF | 0.64 |
| Bovine | None | 1.00 |
| Aortic | 10% Calf Serum | 1.10 |
| Endothelial | EGF | 1.80 |
| Cells | Egressin | 0.80 |

These results in Table III above demonstrate that egressin is not a growth factor but, rather, a cell motility factor as determined by the lack of mitogenic potential on the cells that were tested and an increase in cell movement in the AIG and monolayer assays.

Egressin was also tested for its ability to increase cell numbers. More specifically, egressin prepared as described above was added to the above serum deprived cultures and the cell number determined after 5 days. While the cell number increased approximately four fold in cells cultured in 5.0 ng/ml of EGF or in 10% (v/v) fetal calf serum, there was no increase in cell number in cultures treated with egressin. This also demonstrates that egressin is not a growth factor.

(B) Indirect Mitogenic Assay

Egressin was also tested for an indirect mitogenic effect, i.e., the ability to increase uptake of $^3$H-thymidine into trichloroacetic acid precipitatable material in confluent, density inhibited NRK-49F and bovine aorta cells in the presence of EGF, TGF-$\beta$ or calf serum.

More specifically, all of the cells shown in Table IV below were plated in DMEM containing 10% (v/v) calf serum at $1 \times 10^5$ cells/well. After 5 days at 37° C., the factors were added as described above. TGF-$\beta$ was employed at a concentration of 1.0 ng/ml in DMEM containing 0.5% (v/v) calf serum.

After culturing for 16-18 hours at 37° C., 50 μl of 0.01 μCi/ml of ³H-thymidine was added to each well and the cells were cultured for an additional 8 hours. The cultures were then rinsed twice with DMEM. Next, the cells were rinsed twice with 10% (w/v) trichloroacetic acid at 4° C., and then solubilized with 0.5 ml of 1.0% (w/v) NaOH. The solubilized material was added to 3.0 ml of an aqueous based liquid scintillant (Safety-solve, Research Products Institute) and counted in a scintillation counter. The mitogenic index, expressed as the ratio of cpm incorporated in the presence of added factors/cpm incorporated in cultures receiving no added factors, is shown in Table IV below. All experiments were done on duplicate wells.

TABLE IV

| Cell Type | Indirect Mitogenic Assay | |
|---|---|---|
| | Addition | Mitogenic Index |
| NRK-49F | None | 1.00 |
| | EGF | 8.50 |
| | Egression | 2.10 |
| | TGF-β | 2.20 |
| | Egressin + EGF | 11.30 |
| | Egressin + TGF-β | 11.00 |
| Bovine | None | 1.00 |
| Aortic | EGF | 2.60 |
| Endothelial | Egressin | 0.94 |
| Cells | TGF-β | 0.12 |

The results in Table IV above demonstrate that egressin is an indirect mitogen, i.e., egressin increased thymidine incorporation in contact-inhibited NRK-49F cells in the presence of 10% (v/v) calf serum, and this effect was enhanced by TGF-β and EGF. Egressin lacked any mitogenic effect on the bovine aortic endothelial cells in the presence or absence of TGF-β and did not induce growth of serum-deprived NRK-49F cells.

While this invention has been described in detail and with reference to specific embodiments thereof, it will be apparent to one skilled in the art that various changes and modifications could be made therein without departing from the spirit and scope thereof.

We claim:
1. Essentially pure egressin having the following properties:
   (1) an apparent molecular weight of approximately 10,000 daltons as determined by SDS-PAGE;
   (2) it possesses an overall basic pH;
   (3) it is stable when heated at 56° C. for 30 minutes;
   (4) it is stable at about pH 3.0 to about pH 10.0;
   (5) it is active in inducing a loose colony morphology in normal rat kidney fibroblasts;
   (6) it is active in effecting migration of normal rat kidney epithelial and fibroblast cells out of monolayer colonies thereof;
   (7) is an indirect mitogen; and
   (8) has an approximate relative amino acid composition as follows:

| | | |
|---|---|---|
| ASP | 10.7 | |
| THR | 5.2 | |
| SER | 6.7 | |
| GLU | 14.8 | |
| PRO | N.D. | |
| GLY | 9.8 | |
| ALA | 7.7 | |
| CYS | N.D. | |
| VAL | 5.4 | |
| MET | 1.1 | |
| ILE | 3.5 | |
| LEU | 6.3 | |
| TYR | 1.9 | |
| PHE | 2.8 | |
| LYS | [10] | |
| HIS | 2.3 | |
| TRP | N.D. | |
| ARG | 5.0 | |
| TOTAL | 93.2, | | where the amino acid amounts are measured relative to lysine content.

2. A process for producing egressin comprising the following steps:
   (1) culturing human metastatic melanoma M3827 clone 3 (ATCC No. CRL 9193) in serum-free media;
   (2) collecting the resulting serum-free conditioned media;
   and, additionally, the following steps, which can be carried out in any sequence, except that step (6) is not the first step,
   (3) carrying out molecular weight separation in the presence of 1.0M acetic acid and isolating the approximately 25,000 molecular weight fraction(s) containing egressin activity,
   (4) carrying out cation-exchange separation and isolating the basic fraction(s) containing said egressin activity;
   (5) carrying out hydroxyapitite chromatography and isolating the tightly-bound fraction(s) containing said egressin activity; and
   (6) carrying out hydrophobic separation and isolating the hydrophobic fraction(s) containing said egressin activity,
   wherein a positive result for egressin activity is indicated by inducing a loose colony morphology in normal rat kidney fibroblasts or by effecting migration of normal rat kidney epithelial and fibroblast cells out of monolayer colonies thereof,
so as to obtain egressin purified at least about 10,000 fold.

3. The process for producing egressin as claimed in claim 2, wherein steps (3)-(6) are carried out in the order (3), (4), (5) and (6).

4. A process for producing egressin comprising the following steps:
   (1) culturing human monocytic cell line U937 (ATCC No. CRL 1593) in serum-free media and in the presence of a differentiation-inducing agent;
   (2) collecting the resulting serum-free conditioned media;
   and, additionally, the following steps, which can be carried out in any sequence, except that step (6) is not the first step,
   (3) carrying out cation-exchange separation and isolating the basic fraction(s) containing egressin activity,
   (4) carrying out molecular weight separation in the presence of 1.0M acetic acid and isolating the approximately 25,000 molecular weight fraction(s) containing said egressin activity;
   (5) carrying out cation-exchange separation and isolating the basic fraction(s) containing said egressin activity; and (6) carrying out hydrophobic separation and isolating the hydrophobic fraction(s) containing said egressin activity, wherein a positive result for egressin activity is indicated by inducing a loose colony morphology in normal rat kidney fibroblasts or by effecting migration of normal rat kidney epithelial and fibroblast cells out of monolayer colonies thereof, so as to obtain egressin purified at least about 80,000 fold.

5. The process for producing egressin as claimed in claim 4, wherein said differentiation-inducing agent is selected from the group consisting of 12-O-tetradecanoyl-phorbol 13-acetate and phytohemaglutinin.

6. The process for producing egressin as claimed in claim 4, additionally comprising the following step:

(7) carrying out hydroxyapitite separation and isolating the tightly-bound fraction(s) containing egressin activity, so as to obtain egressin purified at least about 100,000 fold.

7. The process for producing egressin as claimed in claim 4, wherein steps (3)–(6) are carried out in the order (3), (5), (4) and (6) or in the order (3), (5), (6) and (4).

8. The process for producing egressin as claimed in claim 6, wherein steps (3)–(7) are carried out in the order (3), (4), (5), (7) and (6).

9. The process for producing egressin as claimed in claim 2, wherein said egressin has the following properties:
  (1) an apparent molecular weight of approximately 10,000 daltons as determined by SDS-PAGE;
  (2) it possesses an overall basic pH;
  (3) it is stable when heated at 56° C. for 30 minutes;
  (4) it is stable at about pH 3.0 to about pH 10.0;
  (5) it is active in inducing a loose colony morphology in normal rat kidney fibroblasts;
  (6) it is active in effecting migration of normal rat kidney epithelial and fibroblast cells out of monolayer colonies thereof; and
  (7) it is an indirect mitogen.

10. The process for producing egressin as claimed in claim 4, wherein said egressin has the following properties:
  (1) an apparent molecular weight of approximately 10,000 daltons as determined by SDS-PAGE;
  (2) it possesses an overall basic pH;
  (3) it is stable when heated at 56° C. for 30 minutes;
  (4) it is stable at about pH 3.0 to about pH 10.0;
  (5) it is active in inducing a loose colony morphology in normal rat kidney fibroblasts;
  (6) it is active in effecting migration of normal rat kidney epithelial and fibroblast cells out of monolayer colonies thereof; and
  (7) it is an indirect mitogen.

* * * * *